(12) United States Patent
Duckworth et al.

(10) Patent No.: US 6,239,267 B1
(45) Date of Patent: *May 29, 2001

(54) VANILREP1 POLYNUCLEOTIDES AND VANILREP1 POLYPEPTIDES

(75) Inventors: David Malcolm Duckworth, Bishop's Stortford; Philip David Hayes, Cambridge; Helen Jane Meadows, Upminster; John Beresford Davis, Bishop's Stortford, all of (GB)

(73) Assignee: SmithKline Beecham plc, Middlesex (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/197,636

(22) Filed: Nov. 23, 1998

(30) Foreign Application Priority Data

Mar. 12, 1998 (GB) .................................... 9805137
Jul. 20, 1998 (GB) .................................... 9815791
Sep. 3, 1998 (GB) .................................... 9819278

(51) Int. Cl.[7] .................................... C07H 21/04

(52) U.S. Cl. ............................ 536/23.5; 424/93.1; 435/4; 435/320.1; 435/325; 514/44; 536/23.1

(58) Field of Search ............................ 435/4, 325, 320.1; 514/44; 536/23.1, 23.5; 424/93.1

(56) References Cited

U.S. PATENT DOCUMENTS 5,232,684  8/1993  Blumberg et al. .................... 424/1.1

FOREIGN PATENT DOCUMENTS

WO 99/09140  2/1999  (WO) .
WO 99/37675  7/1999  (WO) .

OTHER PUBLICATIONS

Caterina et al. "The capsaicin receptor: a heat–activated ion channel in the pain pathway", Nature, vol. 389, pp. 816–824 (1997).
Accession #T48002. Feb. 24, 1995.
Accession #AA321554. Apr. 18, 1997.
Copy of Partial EP Search Report. EP 98 20 3620 Jun. 1999.
Crystal RG. Science 270:404–410. 1995.*
Orkin SH and Motulsky AG. Report and Recommendations of the Panel to Assess the NIH investment in research of gene therapy, 1995.*
Verma IM and Somia N. Nature 389: 239–242. 1997.*
Adams et al (Genbank accession U91323 ,submitted Mar. 1997).*
Pearce A (Genbank Accession No AL020997, submitted Jan. 9, 1998).*
Gerken et al. (Genbank accession No. L29825, submitted May 23, 1995).*
Chiu (Genbank accession No AC002369 ,submitted Jul. 23, 1997).*
Leube RE et al. J Cell Biol 127:1589–1601. 1994.*
Caterina et al (Genbank accession No. AF029310, submitted Oct. 1997).*

* cited by examiner

Primary Examiner—Karen M. Hauda
Assistant Examiner—M. Shukla
(74) Attorney, Agent, or Firm—William T. Han; Ratner & Prestia; William T. King

(57) ABSTRACT

VANILREP1 polypeptides and polynucleotides and methods for producing such polypeptides by recombinant techniques are disclosed. Also disclosed are methods for utilizing VANILREP1 polypeptides and polynucleotides in therapy, and diagnostic assays for such.

6 Claims, 2 Drawing Sheets

SEQUENCE LISTING

<160> NUMBER OF SEQ ID NOS: 8

<210> SEQ ID NO 1
<211> LENGTH: 4803
<212> TYPE: DNA
<213> ORGANISM: HOMO SAPIENS

<400> SEQUENCE: 1

| | | | | | |
|---|---|---|---|---|---|
| cagcgtcggg | tgcagtttgg | ccggaggttg | cagtgagcag | agattgcccc | attgcactct | 60 |
| agtctgggcg | acagggtgag | acacacacac | acagacacac | acacacacac | acacacacac | 120 |
| acacaagcct | aaacattcra | ggccaggatg | cttgacagat | gttgattcat | aaaaatgaca | 180 |
| aaaagcacaa | aatccaaaat | ctcgtataag | ctcagtggct | gtggcagcga | ggttgaagag | 240 |
| caaaggcagg | ccgggcacct | ggctgatgat | gtgtggaccc | gttgcacagc | agggccccgc | 300 |
| agtgcggtgt | gggtgtgggt | gtgggtgggc | cagtytctgc | cgctcaccct | attccaggga | 360 |
| cacagtctgc | ttggctcttc | tggactgagc | catcctcatc | accgagatcc | tccctgaatt | 420 |
| cagcccacga | cagccacccc | ggccgttttc | cttgttctgt | gtggggaggg | aggcagcgcg | 480 |
| gtggttatca | acctcaccct | gcagaggagg | cacctgaggc | ccagacgcga | ggagggatgg | 540 |
| gtctaaccca | gaaccacaga | tggctctgag | ccggggggcct | gtccaccctc | ccaggccgac | 600 |
| gtcagtggcc | gcaggactgc | ctgggccctg | ctaggcctgc | tcacctctga | ggcctctggg | 660 |
| gtgagaggtt | cagtcctgga | aacacttcag | ttctagggggg | ctggggggcag | cagcaagttg | 720 |
| gagttttggg | gtaccctgct | tcacagggcc | cttggcaagg | agggcaggtg | gggtctaagg | 780 |
| acaagcagtc | cttactttgg | gagtcaaccc | cggcgtggtg | gctgctgcag | gttgcacact | 840 |
| gggccacaga | ggatccagca | aggatgaaga | aatggagcag | cacagacttg | ggggcagctg | 900 |
| cggacccact | ccaaaaggac | acctgcccag | acccctggga | tggagaccct | aactccaggc | 960 |
| cacctccagc | caagcccag | ctctccacgg | ccaagagccg | cacccggctc | tttgggaagg | 1020 |
| gtgactcgga | ggaggctttc | ccgtggatt | gccctcacga | ggaaggtgag | ctggactcct | 1080 |
| gcccgaccat | cacagtcagc | cctgttatca | ccatccagag | gccaggagac | ggccccaccg | 1140 |
| gtgccaggct | gctgtcccag | gactctgtcg | ccgccagcac | cgagaagacc | ctcaggctct | 1200 |
| atgatcgcag | gagtatcttt | gaagccgttg | ctcagaataa | ctgccaggat | ctggagagcc | 1260 |
| tgctgctctt | cctgcagaag | agcaagaagc | acctcacaga | caacgagttc | aaagaccctg | 1320 |
| agacagggaa | gacctgtctg | ctgaaagcca | tgctcaacct | gcacgacgga | cagaacacca | 1380 |
| ccatcccccct | gctcctggag | atcgcgcggc | aaacggacag | cctgaaggag | cttgtcaacg | 1440 |
| ccagctacac | ggacagctac | tacaagggcc | agacagcact | gcacatcgcc | atcgagagac | 1500 |
| gcaacatggc | cctggtgacc | ctcctggtgg | agaacgagc | agacgtccag | gctgcggccc | 1560 |
| atggggactt | ctttaagaaa | accaaagggc | ggcctggatt | ctacttcggt | gaactgcccc | 1620 |
| tgtccctggc | cgcgtgcacc | aaccagctgg | gcatcgtgaa | gttcctgctg | cagaactcct | 1680 |
| ggcagacggc | cgacatcagc | gccagggact | cggtgggcaa | cacggtgctg | cacgccctgg | 1740 |
| tggaggtggc | cgacaacacg | gccgacaaca | cgaagtttgt | gacgagcatg | tacaatgaga | 1800 |
| ttctgatcct | gggggccaaa | ctgcacccga | cgctgaagct | ggaggagctc | accaacaaga | 1860 |
| agggaatgac | gccgctggct | ctggcagctg | ggacgggaa | gatcgggtc | ttggcctata | 1920 |
| ttctccagcg | ggagatccag | gagcccgagt | gcaggcacct | gtccaggaag | ttcaccgagt | 1980 |
| gggcctacgg | gcccgtgcac | tcctcgctgt | acgacctgtc | ctgcatcgac | acctgcgaga | 2040 |

```
agaactcggt gctggaggtg atcgcctaca gcagcagcga gacccctaat cgccacgaca   2100
tgctcttggt ggagccgctg aaccgactcc tgcaggacaa gtgggacaga ttcgtcaagc   2160
gcatcttcta cttcaacttc ctggtctact gcctgtacat gatcatcttc accatggctg   2220
cctactacag gcccgtggat ggcttgcctc cctttaagat ggaaaaaact ggagactatt   2280
tccgagttac tggagagatc ctgtctgtgt taggaggagt ctacttcttt ttccgaggga   2340
ttcagtattt cctgcagagg cggccgtcga tgaagaccct gtttgtggac agctacagtg   2400
agatgctttt ctttctgcag tcactgttca tgctggccac cgtggtgctg tacttcagcc   2460
acctcaagga gtatgtggct tccatggtat tctccctggc cttgggctgg accaacatgc   2520
tctactacac ccgcggtttc cagcagatgg gcatctatgc cgtcatgata gagaagatga   2580
tcctgagaga cctgtgccgt tcatgtttg tctacatcgt cttcttgttc gggttttcca   2640
cagcggtggt gacgctgatt gaagacggga agaatgactc cctgccgtct gagtccacgt   2700
cgcacaggtg gcgggggcct gcctgcaggc cccccgatag ctcctacaac agcctgtact   2760
ccacctgcct ggagctgttc aagttcacca tcggcatggg cgacctggag ttcactgaga   2820
actatgactt caaggctgtc ttcatcatcc tgctgctggc ctatgtaatt ctcacctaca   2880
tcctcctgct caacatgctc atcgccctca tgggtgagac tgtcaacaag atcgcacagg   2940
agagcaagaa catctggaag ctgcagagag ccatcaccat cctggacacg gagaagagct   3000
tccttaagtg catgaggaag gccttccgct caggcaagct gctgcaggtg gggtacacac   3060
ctgatggcaa ggacgactac cggtggtgct tcagggtgga cgaggtgaac tggaccacct   3120
ggaacaccaa cgtgggcatc atcaacgaag acccgggcaa ctgtgagggc gtcaagcgca   3180
ccctgagctt ctccctgcgg tcaagcagag tttcaggcag acactggaag aactttgccc   3240
tggtcccccct tttaagagag gcaagtgctc gagataggca gtctgctcag cccgaggaag   3300
tttatctgcg acagttttca gggtctctga gccagagga cgctgaggtc ttcaagagtc   3360
ctgccgcttc cggggagaag tgaggacgtc acgcagacag cactgtcaac actgggcctt   3420
aggagacccc gttgccacgg ggggctgctg agggaacacc agtgctctgt cagcagcctg   3480
gcctggtctg tgcctgccca gcatgttccc aaatctgtgc tggacaagct gtgggaagcg   3540
ttcttggaag catgggagt gatgtacatc caaccgtcac tgtccccaag tgaatctcct   3600
aacagacttt caggttttta ctcactttac taaacagtkt ggatggtcag tctctactgg   3660
gacatgttag gcccttgttt tctttgattt tattcttttt tttgagacag aatttcactc   3720
ttctcaccca ggctgaaatg cagtggcaca atttggctc cctgcaacct ccgcctcctg   3780
gattccagca attctcctgc ctcggcttcc caagtagctg ggattacagg cacgtgccac   3840
catgtctggc taatttttg tatttttta atagatatgg ggtttcgcca tgttggccag   3900
gctggtctcg aactcctgac ctcaggtgat ccgcccacct cggcctccca aagtgctggg   3960
attacaggtg tgagcctcca cacctggctg ttttctttga ttttattctt tttttttttt   4020
tctgtgagac agagtttcac tcttgttgcc caggctggag tgcagtggtg tgatcttggc   4080
tcactgcaac ttctgcctcc cgggttcaag cgattcttct gcttcagtct cccaagtagc   4140
ttggattaca ggtgagcact accacgcccg gctaattttt gtatttttaa taragacggg   4200
gtttcaccat gttggccagg ctggtctcga actcttgacc tcaggtgatc tgcccgcctt   4260
ggcctcccaa agtgctggga ttacaggtgt gagccgctgc gctcggcctt ctttgatttt   4320
atattattag gagcaaaagt aaatgaagcc caggaaaaca cctttgggaa caaactcttc   4380
```

-continued

```
ctttgatgga aaatgcagag gcccttcctc tctgtgccgt gcttgctcct cttacctgcc      4440
cgggtggttt gggggtgttg gtgtttcctc cctggagaag atgggggagg ctgtcccact      4500
cccagctctg gcagaatcaa gctgttgcag cagtgccttc ttcatccttc cttacgatca      4560
atcacagtct ccagaagatc agctcaattg ctgtgcaggt taaaactaca gaaccacatc      4620 ccaaggtac ctggtaagaa tgtttgaaag atcttccatt tctaggaacc ccagtcctgc       4680
ttctccgcaa tggcacatgc ttccactcca tccatactgg catcctcaaa taaacagata     4740
tgtatacaat aaaaaaaaaa aaaaaaaaaa rrgcggccgc tgaattctag acctgcccgg     4800
gcg                                                                     4803
```

<210> SEQ ID NO 2
<211> LENGTH: 839
<212> TYPE: PRT
<213> ORGANISM: HOMO SAPIENS

<400> SEQUENCE: 2

```
Met Lys Lys Trp Ser Ser Thr Asp Leu Gly Ala Ala Asp Pro Leu
 1               5                  10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
```

```
            290                 295                 300
Phe Val Thr Ser Met Tyr Asn Glu Ile Leu Ile Leu Gly Ala Lys Leu
305                 310                 315                 320
His Pro Thr Leu Lys Leu Glu Glu Leu Thr Asn Lys Lys Gly Met Thr
                325                 330                 335
Pro Leu Ala Leu Ala Ala Gly Thr Gly Lys Ile Gly Val Leu Ala Tyr
            340                 345                 350
Ile Leu Gln Arg Glu Ile Gln Glu Pro Glu Cys Arg His Leu Ser Arg
                355                 360                 365
Lys Phe Thr Glu Trp Ala Tyr Gly Pro Val His Ser Ser Leu Tyr Asp
370                 375                 380
Leu Ser Cys Ile Asp Thr Cys Glu Lys Asn Ser Val Leu Glu Val Ile
385                 390                 395                 400
Ala Tyr Ser Ser Glu Thr Pro Asn Arg His Asp Met Leu Leu Val
                405                 410                 415
Glu Pro Leu Asn Arg Leu Leu Gln Asp Lys Trp Asp Arg Phe Val Lys
            420                 425                 430
Arg Ile Phe Tyr Phe Asn Phe Leu Val Tyr Cys Leu Tyr Met Ile Ile
                435                 440                 445
Phe Thr Met Ala Ala Tyr Tyr Arg Pro Val Asp Gly Leu Pro Pro Phe
450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Arg Gly Ile Gln Tyr Phe
                485                 490                 495
Leu Gln Arg Arg Pro Ser Met Lys Thr Leu Phe Val Asp Ser Tyr Ser
            500                 505                 510
Glu Met Leu Phe Phe Leu Gln Ser Leu Phe Met Leu Ala Thr Val Val
                515                 520                 525
Leu Tyr Phe Ser His Leu Lys Glu Tyr Val Ala Ser Met Val Phe Ser
            530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Ile Val Phe Leu Phe Gly Phe Ser
                580                 585                 590
Thr Ala Val Val Thr Leu Ile Glu Asp Gly Lys Asn Asp Ser Leu Pro
            595                 600                 605
Ser Glu Ser Thr Ser His Arg Trp Arg Gly Pro Ala Cys Arg Pro Pro
    610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Ala Tyr Val Ile Leu Thr Tyr
                660                 665                 670
Ile Leu Leu Leu Asn Met Leu Ile Ala Leu Met Gly Glu Thr Val Asn
                675                 680                 685
Lys Ile Ala Gln Glu Ser Lys Asn Ile Trp Lys Leu Gln Arg Ala Ile
            690                 695                 700
Thr Ile Leu Asp Thr Glu Lys Ser Phe Leu Lys Cys Met Arg Lys Ala
705                 710                 715                 720
```

```
                Phe Arg Ser Gly Lys Leu Leu Gln Val Gly Tyr Thr Pro Asp Gly Lys
                                725                 730                 735

Asp Asp Tyr Arg Trp Cys Phe Arg Val Asp Glu Val Asn Trp Thr Thr
                                740                 745                 750

Trp Asn Thr Asn Val Gly Ile Ile Asn Glu Asp Pro Gly Asn Cys Glu
                                755                 760                 765

Gly Val Lys Arg Thr Leu Ser Phe Ser Leu Arg Ser Ser Arg Val Ser
                                770                 775                 780

Gly Arg His Trp Lys Asn Phe Ala Leu Val Pro Leu Leu Arg Glu Ala
                785                 790                 795                 800

Ser Ala Arg Asp Arg Gln Ser Ala Gln Pro Glu Glu Val Tyr Leu Arg
                                805                 810                 815

Gln Phe Ser Gly Ser Leu Lys Pro Glu Asp Ala Glu Val Phe Lys Ser
                                820                 825                 830

Pro Ala Ala Ser Gly Glu Lys
                                835

<210> SEQ ID NO 3
<211> LENGTH: 4803
<212> TYPE: DNA
<213> ORGANISM: HOMO SAPIENS

<400> SEQUENCE: 3
cagcgtcggg tgcagtttgg ccggaggttg cagtgagcag agattgcccc attgcactct      60
agtctgggcg acagggtgag acacacacac acagacacac acacacacac acacacacac     120
acacaagcct aaacattcra ggccaggatg cttgacagat gttgattcat aaaaatgaca     180
aaaagcacaa aatccaaaat ctcgtataag ctcagtggct gtggcagcga ggttgaagag     240
caaaggcagg ccgggcacct ggctgatgat gtgtggaccc gttgcacagc agggccccgc     300
agtgcggtgt gggtgtgggt gtgggtgggc cagtytctgc cgctcaccct attccaggga     360
cacagtctgc ttggctcttc tggactgagc atcctcatc accgagatcc tccctgaatt      420
cagcccacga cagccacccc ggccgttttc cttgttctgt gtggggaggg aggcagcgcg     480
gtggttatca acctcaccct gcagaggagg cacctgaggc ccagacgacga ggagggatgg    540 gtctaaccca gaaccacaga tggctctgag ccgggggcct gtccaccctc caggccgac     600 gtcagtggcc gcaggactgc ctgggccctg ctaggcctgc tcacctctga ggcctctggg     660
gtgagaggtt cagtcctgga aacacttcag ttctagggg ctgggggcag cagcaagttg     720
gagttttggg gtaccctgct tcacagggcc cttggcaagg agggcaggtg gggtctaagg     780
acaagcagtc cttactttgg gagtcaaccc cggcgtggtg gctgctgcag gttgcacact     840
gggccacaga ggatccagca aggatgaaga aatggagcag cacagacttg ggggcagctg     900
cggacccact ccaaaaggac acctgcccag acccctggg tggagaccct aactccaggc      960
cacctccagc caagcccccag ctctccacgg ccaagagccg cacccggctc tttgggaagg    1020
gtgactcgga ggaggcttc ccggtggatt gccctcacga ggaaggtgag ctggactcct     1080 gccccgaccat cacagtcagc cctgttatca ccatccagag gccaggagac ggccccaccg    1140
gtgccaggct gctgtcccag gactctgtcg ccgccagcac cgagaagacc ctcaggctct    1200
atgatcgcag gagtatcttt gaagccgttg ctcagaataa ctgccaggat ctggagagcc    1260
tgctgctctt cctgcagaag agcaagaagc acytcacaga caacgagttc aaagaccctg    1320
agacagggaa gacctgtctg ctgaaagcca tgctcaacct gcacgacgga cagaacacca    1380
```

-continued

```
ccatcccct gctcctggag atcgcgcggc aaacggacag cctgaaggag cttgtcaacg    1440
ccrgctacac ggacagstac tacaagggcc agacagcact gcacatcgcc atcgagagac   1500
gcaacatggc cctggtgacc ctcctggtgg agaacggagc agacgtccag gctgcggccc   1560
atggggactt ctttaagaaa accaaagggc ggcctggatt ctacttcggt gaactgcccc   1620
tgtccctggc cgcgtgcacc aaccagctgg gcatcgtgaa gttcctgctg cagaactcct   1680
ggcagacggc cgacatcagc gccagggact cggtgggcaa cacggtgctg cacgccctgg   1740
tggaggtggc cgacaacacg gccgacaaca cgaagtttgt gacgagcatg tacaatgaga   1800
ttctgatcct gggggccaaa ctgcacccga cgctgaagct ggaggagctc accaacaaga   1860
agggaatgac gccgctggct ctggcagctg ggacgggaa gatcgggtc ttggcctata    1920
ttctccagcg ggagatccag gagcccgagt gcaggcacct gtccaggaag ttcaccgagt   1980
gggcctacgg gcccgtgcac tcctcgctgt acgacctgtc ctgcatcgac acctgcgaga   2040
agaactcggt gctggaggtg atcgcctaca gcagcagcga gacccctaat cgccacgaca   2100
tgctcttggt ggagccgctg aaccgactcc tgcaggacaa gtgggacaga ttcgtcaagc   2160
gcatcttcta cttcaacttc ctggtctact gcctgtacat gatcatcttc accatggctg   2220
cctactacag gcccgtggat ggcttgcctc cctttaagat ggaaaaaact ggagactatt   2280
tccgagttac tggagagatc ctgtctgtgt taggaggagt ctacttcttt ttccgaggga   2340
ttcagtattt cctgcagagg cggccgtcga tgaagaccct gtttgtggac agctacagtg   2400
agatgctttt ctttctgcag tcactgttca tgctggccac cgtggtgctg tacttcagcc   2460
acctcaagga gtatgtggct tccatggtat tctccctggc cttgggctgg accaacatgc   2520
tctactacac ccgcggtttc cagcagatgg gcatctatgc cgtcatgata gagaagatga   2580
tcctgagaga cctgtgccgt ttcatgtttg tctacatcgt cttcttgttc gggttttcca   2640
cagcggtggt gacgctgatt gaagacggga agaatgactc cctgccgtct gagtccacgt   2700
cgcacaggtg gcgggggcct gcctgcaggc ccccgatag ctcctacaac agcctgtact   2760
ccacctgcct ggagctgttc aagttcacca tcggcatggg cgacctggag ttcactgaga   2820
actatgactt caaggctgtc ttcatcatcc tgctgctggc ctatgtaatt ctcacctaca   2880
tcctcctgct caacatgctc atcgccctca tgggtgagac tgtcaacaag atcgcacagg   2940
agagcaagaa catctggaag ctgcagagag ccatcaccat cctggacacg gagaagagct   3000
tccttaagtg catgaggaag gccttccgct caggcaagct gctgcaggtg gggtacacac   3060
ctgatggcaa ggacgactac cggtggtgct tcagggtgga cgaggtgaac tggaccacct   3120
ggaacaccaa cgtgggcatc atcaacgaag cccgggcaa ctgtgagggc gtcaagcgca   3180
ccctgagctt ctccctgcgg tcaagcagag tttcaggcag acactggaag aactttgccc   3240
tggtcccct tttaagagag gcaagtgctc gagataggca gtctgctcag cccgaggaag   3300
tttatctgcg acagttttca gggtctctga agccagagga cgctgaggtc ttcaagagtc   3360
ctgccgcttc cggggagaag tgaggacgtc acgcagacag cactgtcaac actgggcctt   3420
aggagacccc gttccacgg ggggctgctg agggaacacc agtgctctgt cagcagcctg    3480
gcctggtctg tgcctgccca gcatgttccc aaatctgtgc tggacaagct gtgggaagcg   3540
ttcttggaag catggggagt gatgtacatc caaccgtcac tgtccccaag tgaatctcct   3600
aacagacttt caggttttta ctcactttac taaacagtkt ggatggtcag tctctactgg   3660
gacatgttag gcccttgttt tctttgattt tattctttt tttgagacag aatttcactc    3720
ttctcaccca ggctggaatg cagtggcaca attttggctc cctgcaacct ccgcctcctg   3780
```

-continued

```
gattccagca attctcctgc ctcggcttcc caagtagctg ggattacagg cacgtgccac    3840
catgtctggc taatttttg tattttttta atagatatgg ggtttcgcca tgttggccag     3900
gctggtctcg aactcctgac ctcaggtgat ccgcccacct cggcctccca aagtgctggg    3960
attacaggtg tgagcctcca cacctggctg ttttctttga ttttattctt ttttttttt    4020 tctgtgagac agagtttcac tcttgttgcc caggctggag tgcagtggtg tgatcttggc    4080
tcactgcaac ttctgcctcc cgggttcaag cgattcttct gcttcagtct cccaagtagc    4140
ttggattaca ggtgagcact accacgcccg gctaatttt gtattttaa taragacggg      4200 gtttcaccat gttggccagg ctggtctcga actcttgacc tcaggtgatc tgcccgcctt    4260
ggcctcccaa agtgctggga ttacaggtgt gagccgctgc gctcggcctt ctttgatttt    4320
atattattag gagcaaaagt aaatgaagcc caggaaaaca cctttgggaa caaactcttc    4380 cttttgatgga aaatgcagag gcccttcctc tctgtgccgt gcttgctcct cttacctgcc    4440
cgggtggttt gggggtgttg gtgtttcctc cctggagaag atgggggagg ctgtcccact    4500
cccagctctg gcagaatcaa gctgttgcag cagtgccttc ttcatccttc cttacgatca    4560
atcacagtct ccagaagatc agctcaattg ctgtgcaggt taaaactaca gaaccacatc    4620
ccaaaggtac ctggtaagaa tgtttgaaag atcttccatt tctaggaacc ccagtcctgc    4680
ttctccgcaa tggcacatgc ttccactcca tccatactgg catcctcaaa taaacagata    4740
tgtatacaat aaaaaaaaaa aaaaaaaaaa rrgcggccgc tgaattctag acctgcccgg    4800
gcg                                                                  4803
```

<210> SEQ ID NO 4
<211> LENGTH: 839
<212> TYPE: PRT
<213> ORGANISM: HOMO SAPIENS
<220> FEATURE:
<221> NAME/KEY: UNSURE
<222> LOCATION: (144)(194)(198)

<400> SEQUENCE: 4

```
Met Lys Lys Trp Ser Ser Thr Asp Leu Gly Ala Ala Asp Pro Leu
 1               5                  10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
        50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Xaa
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
```

-continued

```
                165                 170                 175
Leu Leu Glu Ile Ala Arg Gln Thr Asp Ser Leu Lys Glu Leu Val Asn
            180                 185                 190

Ala Xaa Tyr Thr Asp Xaa Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala His Gly Asp Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Ile Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
        355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
        435                 440                 445

Phe Thr Met Ala Ala Tyr Tyr Arg Pro Val Asp Gly Leu Pro Pro Phe
450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Arg Gly Ile Gln Tyr Phe
                485                 490                 495

Leu Gln Arg Arg Pro Ser Met Lys Thr Leu Phe Val Asp Ser Tyr Ser
            500                 505                 510

Glu Met Leu Phe Phe Leu Gln Ser Leu Phe Met Leu Ala Thr Val Val
        515                 520                 525

Leu Tyr Phe Ser His Leu Lys Glu Tyr Val Ala Ser Met Val Phe Ser
    530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Ile Val Phe Leu Phe Gly Phe Ser
            580                 585                 590
```

```
Thr Ala Val Val Thr Leu Ile Glu Asp Gly Lys Asn Asp Ser Leu Pro
        595                 600                 605
Ser Glu Ser Thr Ser His Arg Trp Arg Gly Pro Ala Cys Arg Pro Pro
    610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Ala Tyr Val Ile Leu Thr Tyr
                660                 665                 670
Ile Leu Leu Leu Asn Met Leu Ile Ala Leu Met Gly Glu Thr Val Asn
        675                 680                 685
Lys Ile Ala Gln Glu Ser Lys Asn Ile Trp Lys Leu Gln Arg Ala Ile
    690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
                740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Ser Arg Val Ser
    770                 775                 780
Gly Arg His Trp Lys Asn Phe Ala Leu Val Pro Leu Leu Arg Glu Ala
785                 790                 795                 800
Ser Ala Arg Asp Arg Gln Ser Ala Gln Pro Glu Glu Val Tyr Leu Arg
                805                 810                 815
Gln Phe Ser Gly Ser Leu Lys Pro Glu Asp Ala Glu Val Phe Lys Ser
                820                 825                 830
Pro Ala Ala Ser Gly Glu Lys
        835

<210> SEQ ID NO 5
<211> LENGTH: 432
<212> TYPE: DNA
<213> ORGANISM: HOMO SAPIENS
<220> FEATURE:
<221> NAME/KEY: UNSURE
<222> LOCATION: (83)(89)

<400> SEQUENCE: 5
gagcttctcc ctgcggtcaa gcagagtttc aggcagacac tggaagaact ttgccctggt      60
ccccctttta agagaggcaa gtnctcgana taggcagtct gctcagcccg aggaagttta     120
tctgcgacag ttttcagggt ctctaaagcc agaggacgct gaggtcttca agagtcctgc     180
cgcttccggg gagaagtgag gacgtcacgc agacagcact gtcaacactg ggccttagga     240
gaccccgttg ccacgggggg ctgctgaggg aacaccagtg cttttttcagc agccttgcct    300 gggtctttgc ctgcccagca tgttcccaaa tctgtgctgg acaagctgtg gggaagcgtt     360
cttgggaagc atgggggagt gatgttacat ccaaccgtca ctgtcccaa gttgaatctt      420 ccttaacaga tt                                                         432

<210> SEQ ID NO 6
<211> LENGTH: 65
```

<212> TYPE: PRT
<213> ORGANISM: HOMO SAPIENS
<220> FEATURE:
<221> NAME/KEY: UNSURE
<222> LOCATION: (28)(30)

<400> SEQUENCE: 6

Ser Phe Ser Leu Arg Ser Ser Arg Val Ser Gly Arg His Trp Lys Asn
1               5                   10                  15

Phe Ala Leu Val Pro Leu Leu Arg Glu Ala Ser Xaa Arg Xaa Arg Gln
            20                  25                  30

Ser Ala Gln Pro Glu Glu Val Tyr Leu Arg Gln Phe Ser Gly Ser Leu
            35                  40                  45

Lys Pro Glu Asp Ala Glu Val Phe Lys Ser Pro Ala Ala Ser Gly Glu
        50                  55                  60

Lys
65

<210> SEQ ID NO 7
<211> LENGTH: 3500
<212> TYPE: DNA
<213> ORGANISM: HOMO SAPIENS

<400> SEQUENCE: 7

| | | | | | |
|---|---|---|---|---|---|
| cagcgtcggg | tgcagtttgg | ccggaggttg | cagtgagcag | agattgcccc | attgcactct | 60 |
| agtctgggcg | acagggtgag | acacacacac | acagacacac | acacacacac | acacacacac | 120 |
| acacaagcct | aaacattcra | ggccaggatg | cttgacagat | gttgattcat | aaaaatgaca | 180 |
| aaaagcacaa | aatccaaaat | ctcgtataag | ctcagtggct | gtggcagcga | ggttgaagag | 240 |
| caaaggcagg | ccgggcacct | ggctgatgat | gtgtggaccc | gttgcacagc | agggccccgc | 300 |
| agtgcggtgt | gggtgtgggt | gtgggtgggc | cagtytctgc | cgctcaccct | attccaggga | 360 |
| cacagtctgc | ttggctcttc | tggactgagc | catcctcatc | accgagatcc | tccctgaatt | 420 |
| cagcccacga | cagccacccc | ggccgttttc | cttgttctgt | gtggggaggg | aggcagcgcg | 480 |
| gtggttatca | acctcaccct | gcagaggagg | cacctgaggc | ccagagacga | ggagggatgg | 540 |
| gtctaaccca | gaaccacaga | tggctctgag | ccgggggcct | gtccaccctc | ccaggccgac | 600 |
| gtcagtggcc | gcaggactgc | ctgggccctg | ctaggcctgc | tcacctctga | ggcctctggg | 660 |
| gtgagaggtt | cagtcctgga | aacacttcag | ttctaggggg | ctgggggcag | cagcaagttg | 720 |
| gagttttggg | gtaccctgct | tcacaggggcc | cttggcaagg | agggcaggtg | gggtctaagg | 780 |
| acaagcagtc | cttactttgg | gagtcaaccc | cggcgtggtg | gctgctgcag | gttgcacact | 840 |
| gggccacaga | ggatccagca | aggatgaaga | aatggagcag | cacagacttg | ggggcagctg | 900 |
| cggacccact | ccaaaaggac | acctgcccag | accccctgga | tggagaccct | aactccaggc | 960 |
| cacctccagc | caagccccag | ctctccacgc | caagagccg | cacccggctc | tttgggaagg | 1020 |
| gtgactcgga | ggaggctttc | ccggtggatt | gccctcacga | ggaaggtgag | ctggactcct | 1080 |
| gcccgaccat | cacagtcagc | cctgttatca | ccatccagag | gccaggagac | ggccccaccg | 1140 |
| gtgccaggct | gctgtcccag | gactctgtcg | ccgccagcac | cgagaagacc | ctcaggctct | 1200 |
| atgatcgcag | gagtatcttt | gaagccgttg | ctcagaataa | ctgccaggat | ctggagagcc | 1260 |
| tgctgctctt | cctgcagaag | agcaagaagc | acctcacaga | caacgagttc | aaagaccctg | 1320 |
| agacagggaa | gacctgtctg | ctgaaagcca | tgctcaacct | gcacgacgga | cagaacacca | 1380 |
| ccatccccct | gctcctggag | atcgcgcggc | aaacggacag | cctgaaggag | cttgtcaacg | 1440 |

-continued

```
ccagctacac ggacagctac tacaagggcc agacagcact gcacatcgcc atcgagagac    1500
gcaacatggc cctggtgacc ctcctggtgg agaacggagc agacgtccag gctgcggccc    1560
atggggactt ctttaagaaa accaaagggc ggcctggatt ctacttcggt gaactgcccc    1620
tgtccctggc cgcgtgcacc aaccagctgg gcatcgtgaa gttcctgctg cagaactcct    1680
ggcagacggc cgacatcagc gccagggact cggtgggcaa cacggtgctg cacgccctgg    1740
tggaggtggc cgacaacacg gccgacaaca cgaagtttgt gacgagcatg tacaatgaga    1800
ttctgatcct gggggccaaa ctgcacccga cgctgaagct ggaggagctc accaacaaga    1860
agggaatgac gccgctggct ctggcagctg ggaccgggaa gatcgggtc ttggcctata    1920 ttctccagcg ggagatccag gagcccgagt gcaggcacct gtccaggaag ttcaccgagt    1980
gggcctacgg gcccgtgcac tcctcgctgt acgacctgtc ctgcatcgac acctgcgaga    2040
agaactcggt gctggaggtg atcgcctaca gcagcagcga gacccctaat cgccacgaca    2100
tgctcttggt ggagccgctg aaccgactcc tgcaggacaa gtgggacaga ttcgtcaagc    2160
gcatcttcta cttcaacttc ctggtctact gcctgtacat gatcatcttc accatggctg    2220
cctactacag gcccgtggat ggcttgcctc cctttaagat ggaaaaaact ggagactatt    2280
tccgagttac tggagagatc ctgtctgtgt taggaggagt ctacttcttt ttccgaggga    2340
ttcagtattt cctgcagagg cggccgtcga tgaagaccct gtttgtggac agctacagtg    2400
agatgctttt ctttctgcag tcactgttca tgctggccac cgtggtgctg tacttcagcc    2460
acctcaagga gtatgtggct tccatggtat tctccctggc cttgggctgg accaacatgc    2520
tctactacac ccgcggtttc cagcagatgg gcatctatgc cgtcatgata gagaagatga    2580
tcctgagaga cctgtgccgt ttcatgtttg tctacgtcgt cttcttgttc gggttttcca    2640
cagcggtggt gacgctgatt gaagacggga agaatgactc cctgccgtct gagtccacgt    2700
cgcacaggtg gcgggggcct gcctgcaggc cccccgatag ctcctacaac agcctgtact    2760
ccacctgcct ggagctgttc aagttcacca tcggcatggg cgacctggag ttcactgaga    2820
actatgactt caaggctgtc ttcatcatcc tgctgctggc ctatgtaatt ctcacctaca    2880
tcctcctgct caacatgctc atcgccctca tgggtgagac tgtcaacaag atcgcacagg    2940
agagcaagaa catctggaag ctgcagagag ccatcaccat cctggacacg gagaagagct    3000
tccttaagtg catgaggaag gccttccgct caggcaagct gctgcaggtg gggtacacac    3060
ctgatggcaa ggacgactac cggtggtgct tcagggtgga cgaggtgaac tggaccacct    3120
ggaacaccaa cgtgggcatc atcaacgaag acccgggcaa ctgtgagggc gtcaagcgca    3180
ccctgagctt ctccctgcgg tcaagcagag tttcaggcag acactggaag aactttgccc    3240
tggtccccct ttttaagagag gcaagtgctc gagataggca gtctgctcag cccgaggaag    3300
tttatctgcg acagttttca ggtctctga agccagagga cgctgaggtc ttcaagagtc    3360
ctgccgcttc cggggagaag tgaggacgtc acgcagacag cactgtcaac actgggcctt    3420
aggagacccc gttgccacgg ggggctgctg agggaacacc agtgctctgt cagcagcctg    3480
gcctggtctg tgcctgccca                                                3500
```

<210> SEQ ID NO 8
<211> LENGTH: 839
<212> TYPE: PRT
<213> ORGANISM: HOMO SAPIENS

<400> SEQUENCE: 8

Met Lys Lys Trp Ser Ser Thr Asp Leu Gly Ala Ala Ala Asp Pro Leu

-continued

```
  1               5                   10                  15
Gln Lys Asp Thr Cys Pro Asp Pro Leu Asp Gly Asp Pro Asn Ser Arg
                 20                  25                  30
Pro Pro Pro Ala Lys Pro Gln Leu Ser Thr Ala Lys Ser Arg Thr Arg
                 35                  40                  45
Leu Phe Gly Lys Gly Asp Ser Glu Glu Ala Phe Pro Val Asp Cys Pro
                 50                  55                  60
His Glu Glu Gly Glu Leu Asp Ser Cys Pro Thr Ile Thr Val Ser Pro
 65                  70                  75                  80
Val Ile Thr Ile Gln Arg Pro Gly Asp Gly Pro Thr Gly Ala Arg Leu
                 85                  90                  95
Leu Ser Gln Asp Ser Val Ala Ala Ser Thr Glu Lys Thr Leu Arg Leu
                100                 105                 110
Tyr Asp Arg Arg Ser Ile Phe Glu Ala Val Ala Gln Asn Asn Cys Gln
                115                 120                 125
Asp Leu Glu Ser Leu Leu Leu Phe Leu Gln Lys Ser Lys Lys His Leu
130                 135                 140
Thr Asp Asn Glu Phe Lys Asp Pro Glu Thr Gly Lys Thr Cys Leu Leu
145                 150                 155                 160
Lys Ala Met Leu Asn Leu His Asp Gly Gln Asn Thr Thr Ile Pro Leu
                165                 170                 175
Leu Leu Glu Ile Ala Arg Gln Thr Asp Ser Leu Lys Glu Leu Val Asn
                180                 185                 190
Ala Ser Tyr Thr Asp Ser Tyr Tyr Lys Gly Gln Thr Ala Leu His Ile
                195                 200                 205
Ala Ile Glu Arg Arg Asn Met Ala Leu Val Thr Leu Leu Val Glu Asn
210                 215                 220
Gly Ala Asp Val Gln Ala Ala Ala His Gly Asp Phe Phe Lys Lys Thr
225                 230                 235                 240
Lys Gly Arg Pro Gly Phe Tyr Phe Gly Glu Leu Pro Leu Ser Leu Ala
                245                 250                 255
Ala Cys Thr Asn Gln Leu Gly Ile Val Lys Phe Leu Leu Gln Asn Ser
                260                 265                 270
Trp Gln Thr Ala Asp Ile Ser Ala Arg Asp Ser Val Gly Asn Thr Val
                275                 280                 285
Leu His Ala Leu Val Glu Val Ala Asp Asn Thr Ala Asp Asn Thr Lys
290                 295                 300
Phe Val Thr Ser Met Tyr Asn Glu Ile Leu Ile Leu Gly Ala Lys Leu
305                 310                 315                 320
His Pro Thr Leu Lys Leu Glu Glu Leu Thr Asn Lys Lys Gly Met Thr
                325                 330                 335
Pro Leu Ala Leu Ala Ala Gly Thr Gly Lys Ile Gly Val Leu Ala Tyr
                340                 345                 350
Ile Leu Gln Arg Glu Ile Gln Glu Pro Glu Cys Arg His Leu Ser Arg
                355                 360                 365
Lys Phe Thr Glu Trp Ala Tyr Gly Pro Val His Ser Ser Leu Tyr Asp
                370                 375                 380
Leu Ser Cys Ile Asp Thr Cys Glu Lys Asn Ser Val Leu Glu Val Ile
385                 390                 395                 400
Ala Tyr Ser Ser Ser Glu Thr Pro Asn Arg His Asp Met Leu Leu Val
                405                 410                 415
Glu Pro Leu Asn Arg Leu Leu Gln Asp Lys Trp Asp Arg Phe Val Lys
                420                 425                 430
```

-continued

```
Arg Ile Phe Tyr Phe Asn Phe Leu Val Tyr Cys Leu Tyr Met Ile Ile
        435                 440                 445
Phe Thr Met Ala Ala Tyr Tyr Arg Pro Val Asp Gly Leu Pro Pro Phe
450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Arg Gly Ile Gln Tyr Phe
            485                 490                 495
Leu Gln Arg Arg Pro Ser Met Lys Thr Leu Phe Val Asp Ser Tyr Ser
            500                 505                 510
Glu Met Leu Phe Phe Leu Gln Ser Leu Phe Met Leu Ala Thr Val Val
            515                 520                 525
Leu Tyr Phe Ser His Leu Lys Glu Tyr Val Ala Ser Met Val Phe Ser
            530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Val Val Phe Leu Phe Gly Phe Ser
            580                 585                 590
Thr Ala Val Val Thr Leu Ile Glu Asp Gly Lys Asn Asp Ser Leu Pro
            595                 600                 605
Ser Glu Ser Thr Ser His Arg Trp Arg Gly Pro Ala Cys Arg Pro Pro
            610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
            660                 665                 670
Ile Leu Leu Leu Asn Met Leu Ile Ala Leu Met Gly Glu Thr Val Asn
            675                 680                 685
Lys Ile Ala Gln Glu Ser Lys Asn Ile Trp Lys Leu Gln Arg Ala Ile
            690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
            755                 760                 765
Gly Val Lys Arg Thr Leu Ser Phe Ser Leu Arg Ser Ser Arg Val Ser
            770                 775                 780
Gly Arg His Trp Lys Asn Phe Ala Leu Val Pro Leu Leu Arg Glu Ala
785                 790                 795                 800
Ser Ala Arg Asp Arg Gln Ser Ala Gln Pro Glu Glu Val Tyr Leu Arg
            805                 810                 815
Gln Phe Ser Gly Ser Leu Lys Pro Glu Asp Ala Glu Val Phe Lys Ser
            820                 825                 830
Pro Ala Ala Ser Gly Glu Lys
            835
```

VANILREP1 POLYNUCLEOTIDES AND VANILREP1 POLYPEPTIDES

FIELD OF THE INVENTION

This invention relates to newly identified polypeptides and polynucleotides encoding such polypeptides, to their use in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach as a means to identify genes and gne products as therapeutic targets is rapidly superceding earlier approaches based on 'positional cloning'. A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to VANILREP1, in particular VANILREP1 polypeptides and VANILREP1 polynucleotides, recombinant materials and methods for their production. In another aspect, the invention relates to methods for using such polypeptides and polynucleotides, including the treatment of pain, chronic pain, neuropathic pain, postoperative pain, rheumatoid arhritic pain, neuralgia, neuropathies, algesia, nerve injury, ischaemia, neurodegeneration, stroke, incontinence and inflammatory disorders, hereinafter referred to as "the Diseases", amongst others. In a further aspect, the invention relates to methods for identifying agonists and antagonists/inhibitors using the materials provided by the invention, and treating conditions associated with VANILREP1 imbalance with the identified compounds. In a still further aspect, the invention relates to diagnostic assays for detecting diseases associated with inappropriate VANILREP1 activity or levels.

DESCRIPTION OF THE INVENTION

Figure 1:
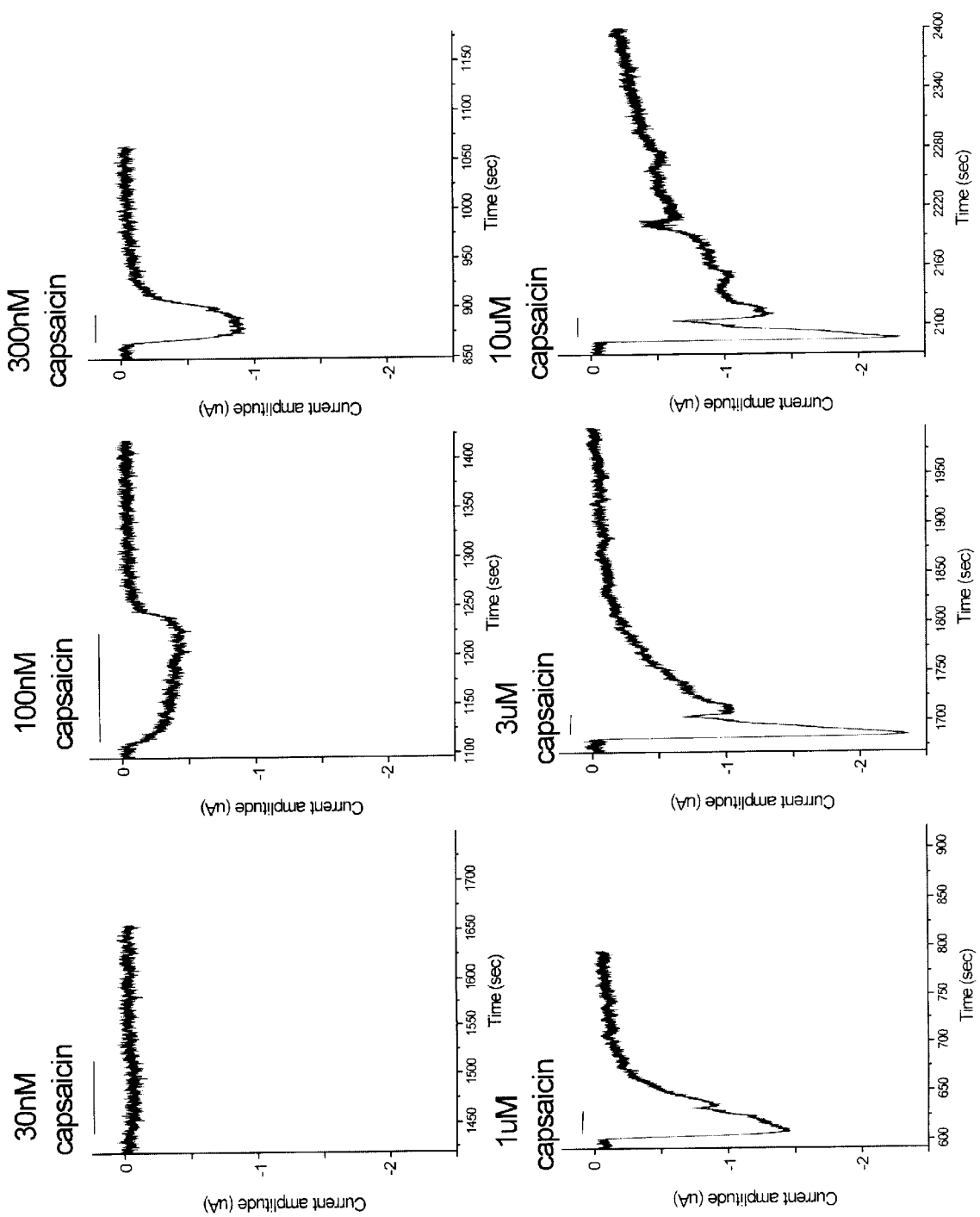
FIG. 1 shows currents evoked from a cell in response to capsaicin over a range of concentrations.

In a first aspect, the present invention relates to VANILREP1 polypeptides. These include the polypeptide of SEQ ID NO:2 and polymorphic variants thereof, for example PVP-1, the polypeptide of SEQ ID NO:8. Such peptides include isolated polypeptides comprising an amino acid sequence which has at least 90% identity, preferably at least 95% identity, more preferably at least 97–99% identity, to that of SEQ ID NO:2 or SEQ ID NO:8 over the entire length of SEQ ID NO:2 or SEQ ID NO:8 respectively. Such polypeptides include those comprising the amino acid of SEQ ID NO:2 or SEQ ID NO:8.

Further peptides of the present invention include isolated polypeptides in which the amino acid sequence has at least 90% identity, preferably at least 95% identity, more preferably at least 97–99% identity, to the amino acid sequence of SEQ ID NO:2 or SEQ ID NO:8, over the entire length of SEQ ID NO:2 or SEQ ID NO:8. Such polypeptides include the polypeptide of SEQ ID NO:2 and SEQ ID NO:8.

Further peptides of the present invention include isolated polypeptides encoded by a polynucleotide comprising the sequence contained in SEQ ID NO:1 or SEQ ID NO:7.

Polypeptides of the present invention are believed to be members of the ion channel family of polypeptides. They are therefore of interest because they are associated with the mechanism of action of capsaicin (a vanilloid compound), a constituent of chilli peppers. Capsaicin elicits a senstation of burning pain by selectively activating sensory neurons that convey information about noxious stimuli to the central nervous system. The channels are permeable to cations and exhibit a notable preferance for divalent cations, particularly calcium ions. The level of calcium ion permeability exceeds that observed for most non-selective cation channels and is similar to values observed for NMDA-type glutamate receptors and alpha7 nicotinic acetylcholine receptors, both of which are noted for this property. These properties are hereinafter referred to as VANILREP1 activity" or VANIL-REP1 polypeptide activity" or "biological activity of VANILREP1". Also included amongst these activities are antigenic and immunogenic activities of said VANILREP1 polypeptides, in particular the antigenic and immunogenic activities of the polypeptides of SEQ ID NO:2 or SEQ ID NO:8. Preferably, a polypeptide of the present invention exhibits at least one biological activity of VANILREP1.

The polypeptides of the present invention may be in the form of the "mature" protein or may be a part of a larger protein such as a precursor or a fusion protein. It is often advantageous to include an additional amino acid sequence which contains secretory or leader sequences, prosequences, sequences which aid in purification such as multiple histidine residues, or an additional sequence for stability during recombinant production.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to VANILREP1 polynucleotides. Such polynucleotides include isolated polynucleotides comprising a nucleotide sequence encoding a polypeptide which has at least 90% identity, preferably at least 95% identity, to the amino acid sequence of SEQ ID NO:2 or SEQ ID NO:8, over the entire length of SEQ ID NO:2 or SEQ ID NO:8, respectively. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 or SEQ ID NO:7, encoding the polypeptide of SEQ ID NO:2 or SEQ ID NO:8, respectively.

Further polynucleotides of the present invention include isolated polynucleotides comprising a nucleotide sequence that has at least 85% identity, preferably at least 90% identity, more preferably at least 95% identity, to a nucleotide sequence encoding a polypeptide of SEQ ID NO:2 or SEQ ID NO:8, respectively, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 85% identity, preferably at least 90% identity, more preferably at least 95% identity, to SEQ ID NO:1 or SEQ ID NO:7, over the entire length of SEQ ID NO:1 or SEQ ID NO:7, respectively. In this regard, polynucleotides which have at least 97% identity are highly preferred, whilst those with at least 98–99% identity are more highly preferred, and those with at least 99% identity are most highly preferred. Such polynucleotides include a polynucleotide comprising the polynucleotide of SEQ ID NO:1 or SEQ ID NO:7, as well as the polynucleotide of SEQ ID NO:1 and SEQ ID NO:7, respectively.

The invention also provides polynucleotides which are complementary to all the above described polynucleotides.

The nucleotide sequences of SEQ ID NO:1 and SEQ ID NO:7 show homology with rat vanilloid receptor VR1(M. J. Caterina et al., Nature 389: 816–824, 1997). The nucleotide sequence of SEQ ID NO:1 is a cDNA sequence and comprises a polypeptide encoding sequence (nucleotide 864 to 3380) encoding a polypeptide of 839 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the ion channel family, having homology and/or structural similarity with rat vanilloid receptor VR1 (M. J. Caterina et al., Nature 389: 816–824, 1997).

The nucleotide sequence of SEQ ID NO:7 is a cDNA sequence and comprises a polypeptide encoding sequence (nucleotide 864 to 3380) encoding a polypeptide of 839 amino acids, the polypeptide of SEQ ID NO:8. The nucleotide sequence encoding the polypeptide of SEQ ID NO:8 may be identical to the polypeptide encoding sequence contained in SEQ ID NO:7 or it may be a sequence other than the one contained in SEQ ID NO:7, which, as a result of the redundancy (degeneracy) of the genetic code, also encodes the polypeptide of SEQ ID NO:8. The polypeptide of the SEQ ID NO:8 is structurally related to other proteins of the ion channel family, having homology and/or structural similarity with rat vanilloid receptor VR1(M. J. Caterina et al., Nature 389: 816–824, 1997).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one VANILREP1 activity.

The present invention also relates to partial or other polynucleotide and polypeptide sequences which were first identified prior to the determination of the corresponding full length sequences of SEQ ID NO:1, SEQ ID NO:7, SEQ ID NO:2 and SEQ ID NO:8.

Accordingly, in a further aspect, the present invention provides for an isolated polynucleotide which:
(a) comprises a nucleotide sequence which has at least 85% identity, preferably at least 90% identity, more preferably at least 95% identity, yet more preferably at least 97–99% identity to SEQ ID NO:3 or SEQ ID NO:5, over the entire length of SEQ ID NO:3 or SEQ ID NO:5, respectively;
(b) has a nucleotide sequence which has at least 85% identity, preferably at least 90% identity, more preferably at least 95% identity, yet more preferably at least 97–99% identity, to SEQ ID NO:3 or SEQ ID NO:5, over the entire length of SEQ ID NO:3 or SEQ ID NO:5, respectively;
(c) the polynucleotide of SEQ ID NO:3 or SEQ ID NO:5; or
(d) a nucleotide sequence encoding a polypeptide which has at least 90% identity, preferably at least 95% identity, more preferably at least 97–99% identity, to the amino acid sequence of SEQ ID NO:4 or SEQ ID NO:6, over the entire length of SEQ ID NO:4 or SEQ ID NO:6, respectively;
as well as the polynucleotides of SEQ ID NO:3 and SEQ ID NO:5.

The present invention further provides for a polypeptide which:
(a) comprises an amino acid sequence which has at least 90% identity, preferably at least 95% identity, more preferably at least 97–99% identity, to that of SEQ ID NO:4 or SEQ ID NO:6, over the entire length of SEQ ID NO:4 or SEQ ID NO:6, respectively;
(b) has an amino acid sequence which has at least 90% identity, preferably at least 95% identity, more preferably at least 97–99% identity, to the amino acid sequence of SEQ ID NO:4 or SEQ ID NO:6, over the entire length of SEQ ID NO:4 or SEQ ID NO:6, respectively;
(c) comprises the amino acid of SEQ ID NO:4 or SEQ ID NO:6; and
(d) is the polypeptide of SEQ ID NO:4 or SEQ ID NO:6;
as well as polypeptides encoded by a polynucleotide comprising the sequence contained in SEQ ID NO:3 or SEQ ID NO:5.

The nucleotide sequences of SEQ ID NO:3 and SEQ ID NO:5, and the peptide sequences encoded thereby are derived from EST (Expressed Sequence Tag) sequences. It is recognised by those skilled in the art that there will inevitably be some nucleotide sequence reading errors in EST sequences (see Adams, M. D. et al, Nature 377 (supp) 3, 1995). Accordingly, the nucleotide sequences of SEQ ID NO:3 and SEQ ID NO:5, and the peptide sequence encoded therefrom, are therefore subject to the same inherent limitations in sequence accuracy.

Polynucleotides of the present invention may be obtained, using standard cloning and screening techniques, from a cDNA library derived from mRNA in cells of human brain, cerebellum, dorsal root ganglia, thymus, leukocytes, placenta, foetal liver spleen and ovary, using the expressed sequence tag (EST) analysis (Adams, M. D., et al. Science (1991) 252:1651–1656; Adams, M. D. et al., Nature, (1992) 355:632–634; Adams, M. D., et al., Nature (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain noncoding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 or SEQ ID NO:8, respectively and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1 or SEQ ID NO:7, respectively, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1 or SEQ ID NO:7,. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process which comprises the steps of screening an appropriate library under stringent hybridization conditions with a labeled probe having the sequence of SEQ ID NO:1 or SEQ ID NO:7, respectively or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1× SSC at about 65° C. Thus the present invention also includes polynucleotides obtainable by screening an appropriate library under stingent hybridization conditions with a labeled probe having the sequence of SEQ ID NO:1 or SEQ ID NO:7, or a fragment thereof.

The skilled artisan will appreciate that, in many cases, an isolated cDNA sequence will be incomplete, in that the region coding for the polypeptide is short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression sytems and to the production of polypeptides of the invention by recombinant techniques. Cell-free translation systems can also be employed to produce such proteins using RNAs derived from the DNA constructs of the present invention.

For recombinant production host cells can be genetically engineered to incorporate expression systems or portions thereof for polynucleotides of the present invention. Introduction of polynucleotides into host cells can be effected by methods described in many standard laboratory manuals, such as Davis et al, Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and or purification.

This invention also relates to the use of polynucleotides of the present invention as diagnostic reagents. Detection of a mutated form of the gene characterised by the polynucleotide of SEQ ID NO:1 or SEQ ID NO:7, respectively which is associated with a dysfunction will provide a diagnostic tool that can add to, or define, a diagnosis of a disease, or susceptibility to a disease, which results from underexpression, over-expression or altered spatial or temporal expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled VANILREP1 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (ee, e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85:4397–4401). In another embodiment, an array of oligonucleotides probes comprising VANILREP1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to the Diseases through detection of mutation in the VANILREP1 gene by the methods described. In addition, such diseases may be diagnosed by methods comprising determining from a sample derived from a subject an abnormally decreased or increased level of polypeptide or MRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagonostic kit which comprises:

(a) a polynucleotide of the present invention, preferably the nucleotide sequence of SEQ ID NO:1 or SEQ ID NO:7, respectively or a fragment thereof;

(b) a nucleotide sequence complementary to that of (a);

(c) a polypeptide of the present invention, preferably the polypeptide of SEQ ID NO:2 or SEQ ID NO:8, respectively or a fragment thereof; or (d) an antibody to a polypeptide of the present invention, preferably to the polypeptide of SEQ ID NO:2 or SEQ ID NO:8, respectively.

It will be appreciated that in any such kit, (a), (b), (c) or (d) may comprise a substantial component. Such a kit will be of use in diagnosing a disease or suspectability to a disease, particularly pain, chronic pain, neuropathic pain, postoperative pain, rheumatoid arthritic pain, neuralgia, neuropathies, algesia, nerve injury, ischaemia, neurodegeneration, stroke, incontinence and inflammatory disorders, amongst others.

The nucleotide sequences of the present invention are also valuable for chromosome localisation. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Jolms Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The gene of the present invention maps to human chromosome 17p13. The nucleotide sequences of the present invention are also valuable for tissue localisation. Such techniques allow the determination of expression patterns of the human VANILREP1 polypeptides in tissues by detection of the mRNAs that encode them. These techniques include in situ hybridziation techniques and nucleotide amplification techniques, for example PCR. Such techniques are well known in the art. Results from these studies provide an indication of the normal functions of the polypeptides in the organism. In addition, comparative studies of the normal expression pattern of human VANILREP1 mRNAs with that of mRNAs encoded by a human VANILREP1 gene provide valuable insights into the role of mutant human VANILREP1 polypeptides, or that of inappropriate expression of normal human VANILREP1 polypeptides, in disease. Such inappropriate expression may be of a temporal, spatial or simply quantitative nature.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-ell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgGI, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for one or more biological functions, including one or more disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2):Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring VANILREP1 activity in the mixture, and comparing the VANILREP1 activity of the mixture to a standard. Fusion proteins, such as those made from Fc portion and VANILREP1 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;
(b) a recombinant cell expressing a polypeptide of the present invention;
(c) a cell membrane expressing a polypeptide of the present invention; or
(d) antibody to a polypeptide of the present invention;
which polypeptide is preferably that of SEQ ID NO:2 or SEQ ID NO:8.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;
(b) deducing the three-dimensional structure for the likely reactive or binding site(s) of an agonist, antagonist or inhibitor;
(c) synthesing candidate compounds that are predicted to bind to or react with the deduced binding or reactive site; and
(d) testing whether the candidate compounds are indeed agonists, antagonists or inhibitors.

It will be further appreciated that this will normally be an iterative process.

In a further aspect, the present invention provides methods of treating abnormal conditions such as, for instance, pain, chronic pain, neuropathic pain, postoperative pain, rheumatoid arthritic pain, neuralgia, neuropathies, algesia, nerve injury, ischaemia, neurodegeneration, stroke, incontinence and inflammatory disorders, related to either an excess of, or an under-expression of, VANILREP1 polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the VANILREP1 polypeptide.

In still another approach, expression of the gene encoding endogenous VANILREP1 polypeptide can be inhibited using expression blocking techniques. Known such techniques involve the use of antisense sequences, either internally generated or externally administered (see, for example, O'Connor, J Neurochem (1991) 56:560 in Oligodeoxynucleotides as Antisense Inhibitors of Gene Expression, CRC Press, Boca Raton, Fla. (1988)). Alternatively, oligonucleotides which form triple helices ("triplexes") with the gene can be supplied (see, for example, Lee et al., Nucleic Acids Res (1979) 6:3073; Cooney et al., Science (1988) 241:456; Dervan et al., Science (1991) 251:1360). These oligomers can be administeredper se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesised with these or other modified backbones also form part of the present invention.

In addition, expression of the human VANILREP1 polypeptide may be prevented by using ribozymes specific to the human VANILREP1 mRNA sequence. Ribozymes are catalytically active RNAs that can be natural or synthetic (see for example Usman, N, et al., Curr. Opin. Struct. Biol (1996) 6(4), 527–33.) Synthetic ribozymes can be designed to specifically cleave human VANILREP1 mRNAs at selected positions thereby preventing translation of the human VANILREP1 mRNAs into functional polypeptide. Ribozymes may be synthesised with a natural ribose phosphate backbone and natural bases, as normally found in RNA molecules. Alternatively the ribosymes may be synthesised with non-natural backbones to provide protection from ribonuclease degradation, for example, 2'-O-methyl RNA, and may contain modified bases.

For treating abnormal conditions related to an under-expression of VANILREP1 and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of VANILREP1 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex Vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as those in the GCG and Lasergene software packages. Accordingly, in a further aspect, the present invention provides for a computer readable medium having stored thereon a polynucleotide comprising the sequence of SEQ ID NO:1 or SEQ ID NO:7 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A ariety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, pgs. 1–12 in Post-translational Covalent Modification of Proteins, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Post-translational Modifications and Aging", Ann NY Acad Sci (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below.

A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAS TManual*, Altschul, S., et al., NCBI NLM NIH Bethesda, MD 20894; Altschul, S., et al., *J. Mol Biol.* 215: 403–410 (1990). The well known Smith Waterman algorithm may also be used to determine identity.

Preferred parameters for polypeptide sequence comparison include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970)

Comparison matrix: matches=+10, mismatch=0

Gap Penalty: 50

Gap Length Penalty: 3
Available as: The "gap" program from Genetics Computer Group, Madison WI. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y)$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (xa \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species, and "paralog" meaning a functionally similar sequence when considered within the same species.

"Fusion protein" refers to a protein encoded by two, often unrelated, fused genes or fragments thereof In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

EXAMPLE

Example 1

Electrophysiological Studies

*Xenopus laevis* oocyte removal and dissociation were performed. Injections of cDNA for VANILREP1 were made into the nuclei of defolliculated oocytes (1.5 ng cDNA/oocyte). After injection the oocytes were incubated between 19–22° C. in modified Barth's solution (MBS) plus gentamycin (0.1 mg/ml, pH 7.4) and used for electrophysiological recordings within 24 days.

For electrophysiological recordings oocytes were placed in a recording chamber and continuously perfused with a solution containing in mM: NaCl 88, KCl 1, $NaHCO_3$ 2.4, HEPES 15, $MgCl_2$ 1, $BaCl_2$ 0.1. (14 ml $min^{-1}$). Solution was applied using large bore tubing (internal diameter 1.5 mm) which facilitated rapid solution exchange (half-time 350–1000 ms). Oocytes were held under voltage clamp at −60 mV using the two-electrode voltage-clamp technique. Electrodes were low resistance (0.5–3 MΩ) and were filled with 3 M KCl.

Figure 2:
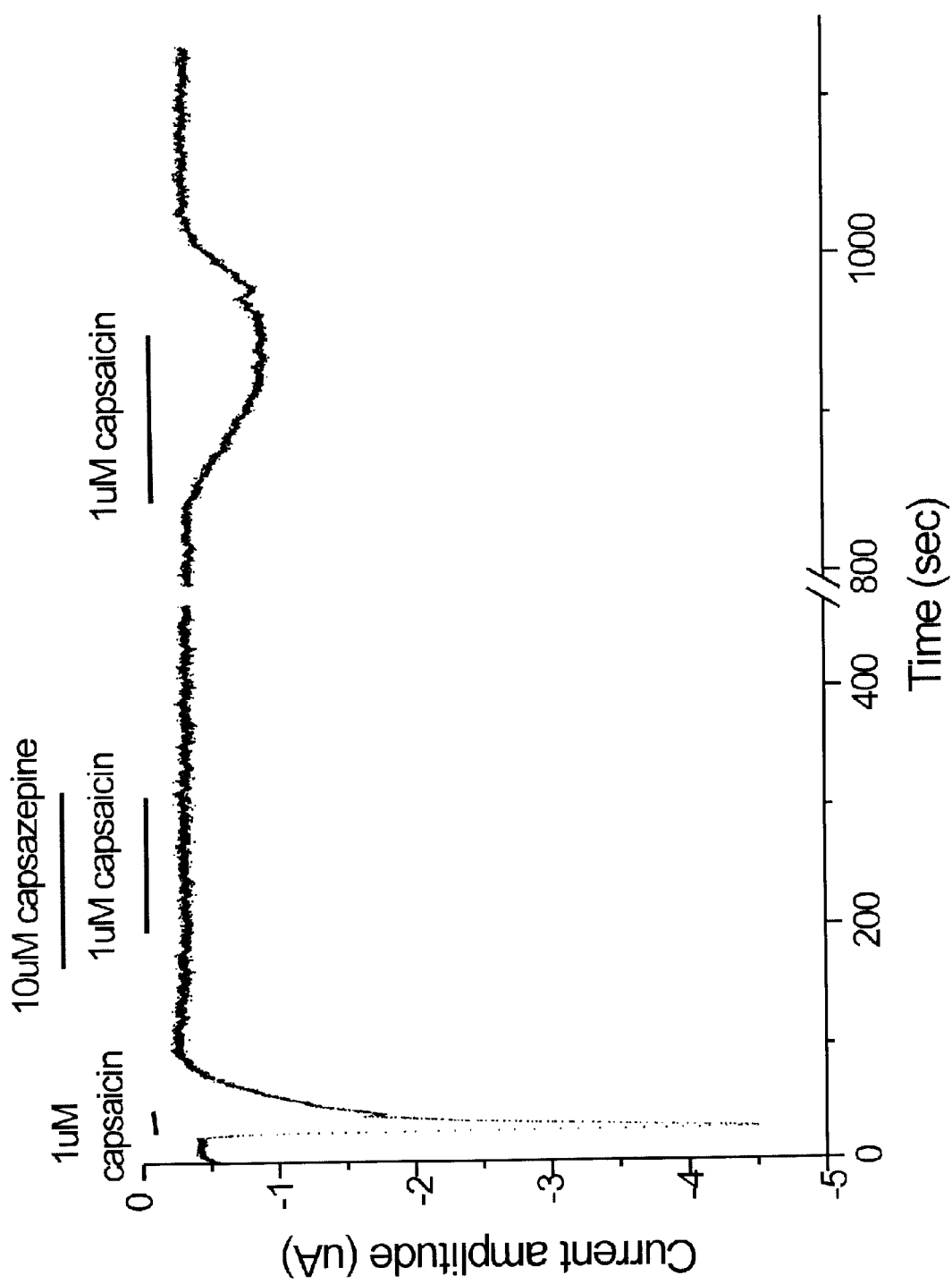
FIG. 2 shows inhibition of the capsaicin evoked response (1 uM) by capsazepine (10 uM). The inhibition is reversible with extended washing.

Currents were evoked in response to application of capsaicin applied through the perfusion system until the maximum current amplitude was reached. FIG. 1 shows currents evoked from a cell in response to capsaicin over a range of concentrations. FIG. 2 shows inhibition of the capsaicin evoked response (1) by capsazepine (10 uM). The inhibition is reversible with extended washing.

What is claimed is:

1. An isolated polynucleotide comprising the nucleotide sequence of SEQ ID NO:1.

2. An isolated polynucleotide consisting of the nucleotide sequence of SEQ ID NO:1.

3. An isolated polynucleotide that is RNA corresponding to the isolated polynucleotide set forth in SEQ ID NO:1.

4. An isolated polynucleotide that is fully complementary to the nucleotide sequence of SEQ ID NO:1.

5. An isolated polynucleotide comprising the nucleotide sequence of SEQ ID NO:7.

6. An isolated polynucleotide comprising the nucleotide sequence of SEQ ID NO:3.

* * * * *